United States Patent
Hooven et al.

(10) Patent No.: US 10,449,293 B2
(45) Date of Patent: Oct. 22, 2019

(54) INJECTION NEEDLE, INJECTION APPARATUS EMPLOYING SAME AND METHOD OF MAKING

(71) Applicant: Enable Injections, Inc., Cincinnati, OH (US)

(72) Inventors: Michael D. Hooven, Cincinnati, OH (US); Matthew J. Huddleston, Loveland, OH (US); David Stefanchik, Morrow, OH (US)

(73) Assignee: Enable Injections, Inc., Cincinnati, OH (US)

( * ) Notice: Subject to any disclaimer, the term of this patent is extended or adjusted under 35 U.S.C. 154(b) by 0 days.

(21) Appl. No.: 15/559,750

(22) PCT Filed: Mar. 2, 2016

(86) PCT No.: PCT/US2016/020331
§ 371 (c)(1),
(2) Date: Sep. 19, 2017

(87) PCT Pub. No.: WO2016/153747
PCT Pub. Date: Sep. 29, 2016

(65) Prior Publication Data
US 2018/0043107 A1    Feb. 15, 2018

Related U.S. Application Data

(60) Provisional application No. 62/136,057, filed on Mar. 20, 2015.

(51) Int. Cl.
| A61M 5/168 | (2006.01) |
| A61M 5/158 | (2006.01) |
| A61M 5/32  | (2006.01) |

(52) U.S. Cl.
CPC ........ *A61M 5/16813* (2013.01); *A61M 5/158* (2013.01); *A61M 5/16877* (2013.01); *A61M 5/329* (2013.01); *A61M 2207/00* (2013.01)

(58) Field of Classification Search
CPC .............. A61M 5/329; A61M 5/16813; A61M 5/16804; A61M 5/16877; A61M 5/3297;
(Continued)

(56) References Cited

U.S. PATENT DOCUMENTS

| 4,766,906 A * | 8/1988 | Wang ................. A61B 10/0283 |
| | | 600/566 |
| 5,201,712 A * | 4/1993 | Bryant ................. A61M 25/00 |
| | | 604/164.02 |

(Continued)

OTHER PUBLICATIONS

International Search Report dated Jun. 14, 2016, from the Korean Intellectual Property Office for International Application No. PCT/US2016/020331.

(Continued)

*Primary Examiner* — Jenna Zhang
(74) *Attorney, Agent, or Firm* — Cook Alex Ltd.; R. Blake Johnston

(57) ABSTRACT

A fluid injection needle has a relatively precision fluid flow path. The needle comprises a needle shaft and a sizing shaft axially extending within the needle shaft lumen a selected distance distal of a fluid entry port into the lumen. The sizing shaft has a cross-sectional size smaller than the lumen to define a fluid flow path between the sizing shaft and the needle shaft. An injection device employing such an injection needle and a method of making such a needle are also disclosed.

8 Claims, 4 Drawing Sheets

(58) Field of Classification Search
CPC .................. A61M 5/168; A61M 5/158; A61M 2025/0004
USPC ............. 604/164.01, 164.02, 164.13, 170.03
See application file for complete search history.

(56) References Cited

U.S. PATENT DOCUMENTS

| | | | |
|---|---|---|---|
| 5,598,973 A | 2/1997 | Weston | |
| 5,897,497 A * | 4/1999 | Fernandez | A61M 25/0662 600/435 |
| 6,569,128 B1 * | 5/2003 | Christensen | A61M 5/16804 604/244 |
| 7,025,329 B2 | 4/2006 | Winter | |
| 2005/0263615 A1 | 12/2005 | Kriesel et al. | |
| 2006/0178646 A1 * | 8/2006 | Harris | A61M 5/3286 604/268 |
| 2006/0206055 A1 | 9/2006 | Ice | |
| 2013/0116556 A1 * | 5/2013 | Racz | A61M 5/158 600/431 |
| 2013/0237958 A1 * | 9/2013 | Arrigo | A61M 25/0102 604/506 |
| 2014/0303550 A1 * | 10/2014 | Williams | A61M 5/329 604/26 |

OTHER PUBLICATIONS

Written Opinion dated Jun. 14, 2016, from the Korean Intellectual Property Office for International Application No. PCT/US2016/020331.

* cited by examiner

INJECTION NEEDLE, INJECTION APPARATUS EMPLOYING SAME AND METHOD OF MAKING

RELATED APPLICATION

This application claims the benefit of and priority to U.S. Provisional Patent Application Ser. No. 62/136,057, filed Mar. 20, 2015, which is hereby incorporated herein by reference.

FIELD OF THE DISCLOSURE

The subject matter of the present application relates generally to medical fluid injection needles and, more specifically, to needles that provide relatively accurate and predictable flow rates, as well as injection devices employing such needles and methods of making such needles.

BACKGROUND

Medical injection needles are typically formed by continuously extruding a suitable metal, such as stainless steel, to form the shaft of the needle with a suitable outside diameter and an inner bore or lumen size also of prescribed diameter. The extruded material is cut to length and ground at one end to form a piercing point for insertion through the skin of a subject.

While such needles work fine for many applications where the requirements for injection flow rates and injection duration are not demanding, it is sometimes necessary, for a variety of reasons, to control the injection flow rate and/or injection duration or delivery time relatively precisely. For example, the injection duration can impact the pain associated with the injection, and slower flow rates or longer duration tend to be less painful. The flow rate and time of injection also may be significant to achieve better medical results of drug diffusion or absorption by the subject. There may also be practical factors such as patient mobility and age that impact the need for improved control of flow rate and/or injection time.

There are numerous factors or variables that can play a role in medical injection duration and flow rates. As examples only, drug delivery time and/or flow rates can vary with the size (diameter) of the needle shaft and the inside lumen, the viscosity of the drug, biologic or other injectable medicament, and the injection pressure. Even for a given medicament at a given temperature, the injection flow rate and duration can vary more than desired with standard injection needles.

One of the reasons for the variability is that the size of the lumen itself can vary significantly as between different batches of extruded needle shaft material. While the lumen is typically consistent within a given extrusion batch, it can vary significantly as between batches. Even the most carefully and precisely extruded needle material can vary significantly in lumen size—particularly as between different batches of needle shaft material. It is understood that due to the extrusion process itself, the outside diameter of the needle is much more accurately and predictably controlled than the inner diameter of the needle lumen. For example, the outer diameter may be controlled within about 0.001 inches.

It is the lumen size, however, that is particularly relevant to fluid flow, because even small variations can affect flow rates and injection duration. This is due to the physics of fluid flow through a lumen, as set forth, for example, in Poiseuille's Law. Poiseuille's law indicates that volume flow rate through a lumen is proportional to lumen radius taken to the fourth power (or $R^4$), so small variations in the lumen size can make a large difference in flow rates at a given pressure and lumen length.

Accordingly, the one aspect of the present subject matter relates to injection needles, methods of making injection needles and injection devices employing such needles, which provide more accurate flow rate and injection duration, and reduce the flow variability as between needles fashioned from different extrusion batches, and potentially even as between individual needles of the same batch.

SUMMARY

In accordance with one aspect of the present subject matter, a fluid injection needle is provided having a precision fluid flow path that provides reduced variability in injection delivery time or duration and injection flow rate, other factors being equal. For purposes of this description, precision fluid flow path means a fluid flow path that is substantially predictable for flow rates and injection times and provides less variability due to lumen size variation, other factors being equal. A precision fluid flow path as used herein does not require or imply exactitude and does not require zero tolerance or variation.

In accordance with this particular aspect, the fluid injection needle includes an elongated needle shaft terminating in a distal end including a piercing point for piercing the skin of a subject. The needle shaft includes an axially extending bore defining a fluid flow lumen extending between a distal fluid injection port and a proximal fluid entry port. A sizing shaft axially extends within the lumen a selected distance distal of the fluid entry port. The sizing shaft has a cross-sectional size smaller than the lumen to define a fluid flow path in the lumen and between the sizing shaft and the needle shaft. Additional aspects of such a fluid injection needle are set forth in the attached claims and in the following more detailed description.

In accordance with another aspect, a medical fluid injection device provided including a housing containing a medical fluid reservoir for containing a medical fluid and an injection needle carried by the housing. The injection needle includes an elongated needle shaft terminating in a distal end including a piercing point for piercing the skin of a subject. The needle shaft includes an axially extending bore defining a fluid flow lumen extending between a distal fluid injection port and a proximal fluid entry port. The injection device includes a fluid pathway communicable between the reservoir and fluid entry port. A sizing shaft axially extends within the lumen a selected distance distal of the fluid entry port. The sizing shaft has a cross-sectional size smaller than the lumen to define a fluid flow path in the lumen between the sizing shaft and the needle shaft.

In yet another aspect of the present subject matter, a method of making a fluid injection needle having a precision fluid flow path is disclosed. The method includes providing an elongated needle shaft terminating in a distal end including a piercing point for piercing the skin of a subject, the needle shaft including an axially extending bore defining a fluid flow lumen extending between a distal fluid injection port and a proximal fluid entry port. The method also includes placing a sizing shaft extending axially in the lumen a selected distance distal of the fluid entry port, the sizing shaft having a cross-sectional size smaller than the lumen to define a fluid flow path in the lumen between the sizing shaft and the lumen surface.

This method may be used to make injection needles having relatively precision flow paths from a given batch of needle shaft material or as between individual needles if desired. For such purposes, the method may include including flowing fluid through the fluid flow path at a selected pressure and determining the fluid flow rate, comparing the determined fluid flow rate to a desired fluid flow rate, replacing the sizing shaft within the shaft lumen with a sizing shaft of different size and/or changing the location of the sizing shaft within the lumen and repeating the steps of flowing, determining, replacing and/or changing until the determined flow rate is within a selected range of the desired fluid flow rate. If desired, the location and size of the sizing shaft determined above can then be used to make other injection needles from the same batch of needle shaft material, employing the same size and location of sizing shaft without the need for further individual needle testing in order to supply an injection needle with a precision fluid flow path.

BRIEF DESCRIPTION OF THE DRAWINGS

The subject matter of this description is illustrated, for purposes of explanation and not limitation, in the attached drawings, of which.

DETAILED DESCRIPTION

Figure 1:
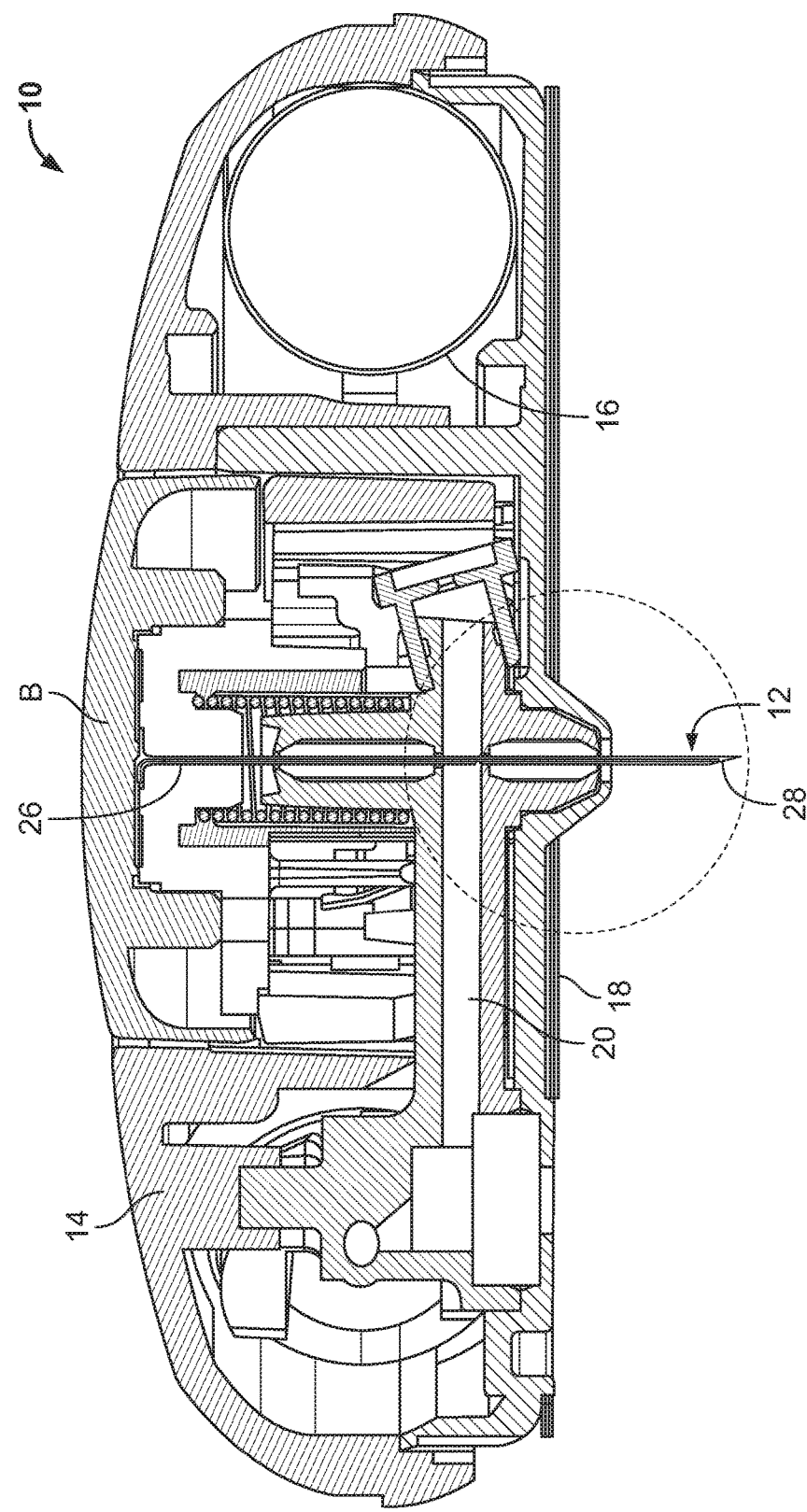
FIG. 1 is cross-sectional view of an exemplary injection device embodying an injection needle in accordance with one aspect the subject matter described herein.

FIG. 1 illustrates one type of medical fluid or medicament injection device 10 employing an injection needle 12 in accordance with the subject matter of this description. This injection device and others are described in detail in PCT International Application No. PCT/US2014/042627, entitled Vial Transfer and Injection Apparatus and Method, which published as PCT Publication No. WO2014204894, on Dec. 24, 2014, and is hereby incorporated by reference in its entirety.

The illustrated injection device 10 in intended to be wearable during the injection and has a housing 14, which contains a medicament reservoir in the form of an arcuate pre-filled elastomeric bladder 16. The housing has skin contacting surface 18 on the underside, with an adhesive that holds the device against the skin of a subject during injection. The housing mounts the injection needle 12 so that it is movable between a retracted position and an extended injection position. The housing also contains associated flow control apparatus that allows a user to activate the device for injection into a subject (typically a human patient) as described in the above PCT application.

As can be seen in FIG. 1, the housing includes a fluid flow passageway 20 that extends between the bladder 16 and the injection needle 12. As may be seen more clearly in the enlarge view of FIG. 2, the injection needle 12 is an assembly of needle shaft 22 and a sizing member 24. The needle shaft is elongated, and extends from a generally proximal end portion 26 to a distal end portion 28.

The needle shaft 22 is typically metallic and, as explained earlier, may be formed by extrusion of stainless steel or other suitable material. The needle shaft is hollow and has an axially extending bore that forms a lumen 30 that extends the length of the needle in the illustrated version. The illustrated needle has a side port 32 that extends through the needle wall and provides open flow communication between the flow path 20 and needle lumen 30 when the needle is in the injection position. The distal end portion of the needle is shaped, usually by grinding, to form a sharp piercing point 34 for piercing the subject's skin. The illustrated lumen extends the full length of the needle and has a discharge or injection port 36 at the distal end. It should be noted that the needle shaft could have a fluid entry port at any desired location, such as an axial opening directly into the proximal end of the needle shaft, or have a fluid injection port at a location other than the distal end, such as a side exit port. In theory, the lumen only needs to extend between the fluid entry port into the lumen and the injection port.

The needle shaft 22 and lumen 30 are typically circular in cross-sectional shape and the needle has an outside diameter or OD and an inside diameter or ID, which is the lumen diameter. It was pointed out above that during manufacture, there is usually much less predictability in the size of the ID than in the OD, and this can create unwanted and unpredictable variation in the injection fluid flow rates and flow duration as between different batches or lots of extruded needle shaft stock. Typically the ID will not vary significantly in a given batch, but can vary significantly between different batches even though no difference may be intended by the manufacturer.

In accordance with the present subject matter a precision fluid flow path can be provided through the needle despite the variation and unpredictability of lumen diameter as between different batches or lots of extruded needle shaft material, and further between as between individual needles if so desired. Specifically, in accordance with one aspect of this subject matter, an elongated sizing member or shaft 24 may be inserted or otherwise positioned, preferably at a fixed location, in the needle shaft lumen 30. The sizing member may be of any suitable cross-sectional shape of material and may be solid or hollow. It may be centered within the lumen so as to extend along the lumen axis or may be off-center with the lumen the sizing member may be supported in a fixed location by a portion of the injection device or may be bonded, welded or otherwise secured to the needle shaft.

Figure 2:
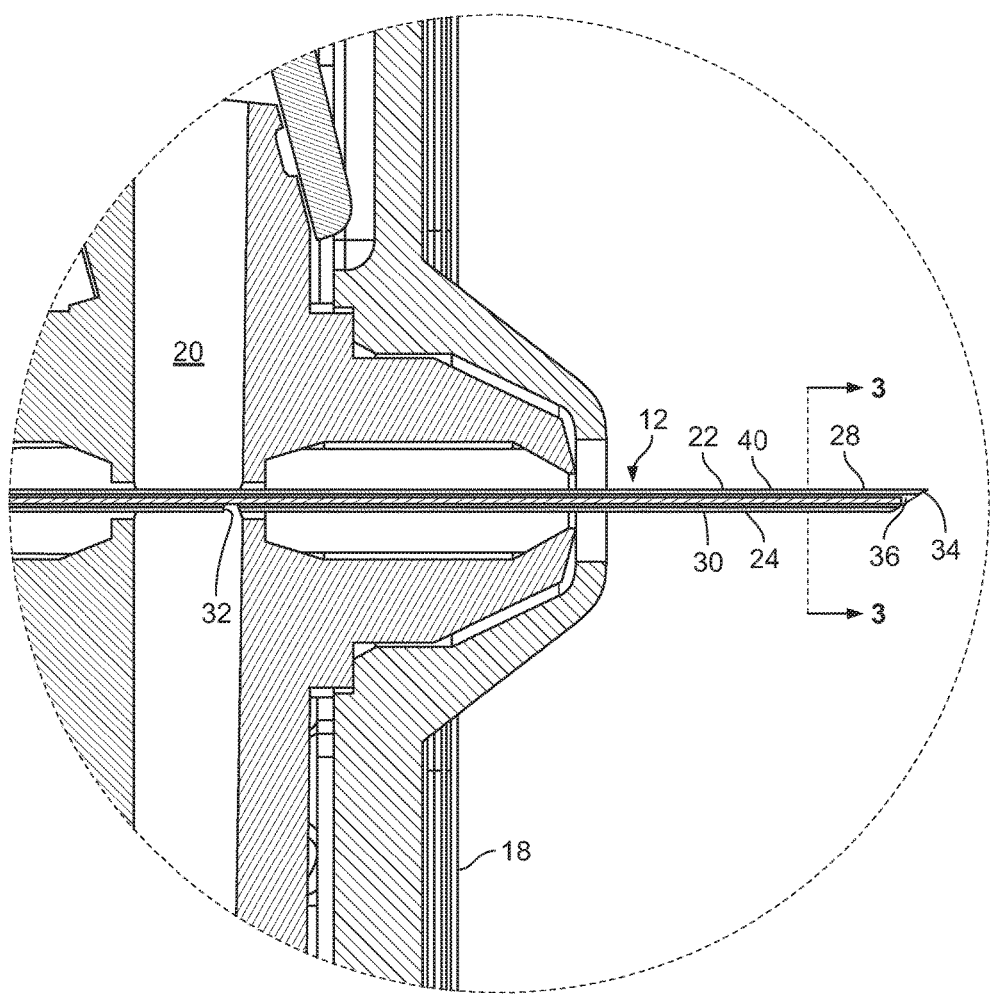
FIG. 2 is an enlarged isolated view of a portion of FIG. 1.
Figure 3:
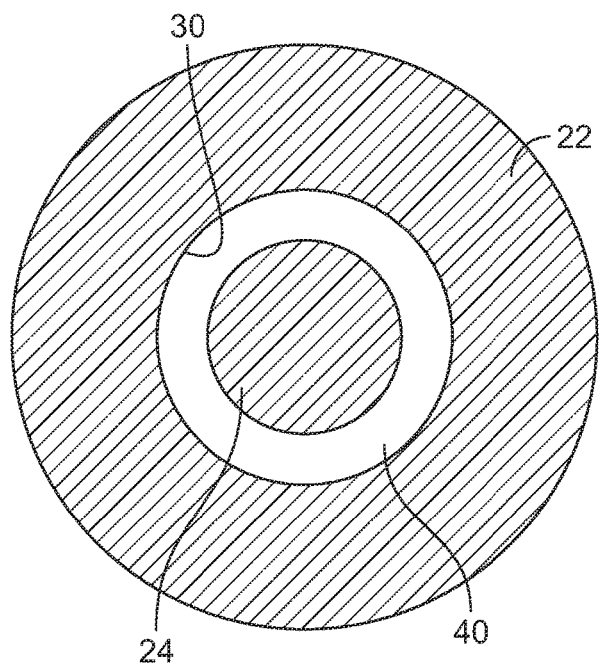
FIG. 3 is a cross-sectional view taken along line 3-3 of FIG. 2.

In one illustrated embodiment, as shown in FIG. 3, the sizing member is a solid elongated metal wire extruded of stainless steel or other suitable material such as plastic material and is positioned in the lumen so that it extends a selected distance distal of the side port 32 (see FIG. 2). The illustrated sizing member is circular in cross-sectional shape with an OD that takes advantage of the characteristic of extrusion to provide a diameter that is relatively predictable and not subject to substantial variation. The sizing member is, however, of smaller cross-sectional size than the lumen so as to define a fluid flow path 40 in the space between the outer surface of the sizing member and the surface of the needle shaft lumen. While typically extruded in circular cross-sectional shape, the needle shaft 22 and flow lumen 30 do not need to be circular, and nor does the sizing member 24. Further, the sizing member does not need to be centered within the lumen and can be offset.

As can be seen in FIG. 3, in accordance with the present subject matter the fluid flow path 40 may be a precision flow path of reasonably predictable and reduced variability in fluid flow rate and injection duration, other factors being equal. More specifically, for a given needle shaft or batch of extruded needle shaft material, the present subject matter provides a method or process that creates a precision flow path 40 in the injection needle. More specifically, the method contemplates a means for gross flow rate adjustment if required and a means for fine flow rate adjustment if required or a combination of those.

For example, a needle shaft may be evaluated by flowing a selected fluid through the lumen, between the inlet port and injection port, at a selected fluid pressure and temperature. The flow rate may be determined or measured, such as by accumulating the fluid passing though the needle over a particular time period and calculating the flow rate. If the measured or determined flow rate is significantly larger than a desired flow rate, the flow rate may be adjusted in a relatively gross amount by placing within the needle lumen a sizing member so that it extends a certain distance distal of the fluid inlet port in the needle shaft and occupies a portion of the lumen. The cross-sectional size or diameter of the sizing member selected may be varied or chosen based on much the determined flow rate differs from the desired flow rate, and relatively larger or gross flow rate adjustments may be made by varying the size of the sizing member selected. For example, if the initial measured flow rate is deemed significantly larger than the desired flow rate, a relatively larger sizing member may be selected to occupy a significant portion of the lumen. The steps of flowing fluid at a selected pressure and determining the flow rate are then repeated and compared to the desired flow rate. If the difference between measured and desired flow rates remains large, the sizing member may be removed and replaced by a larger sizing member to provide larger flow rate adjustment, and the steps of flowing the fluid at a selected pressure' determining the flow rate and replacing the sizing member repeated until the desired and determined flow rates more closely approximate each other.

Figure 4:
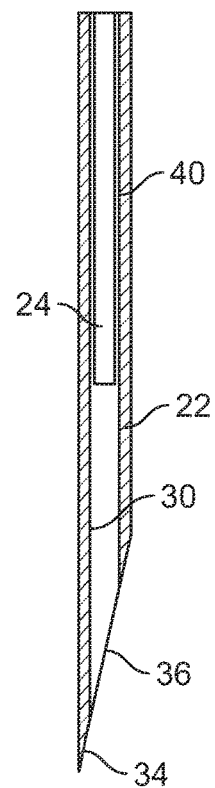
FIG. 4 is a cross-sectional view of an injection needle employing an aspect of the present subject matter.

At this stage, a finer flow rate adjustment may be performed. As shown in FIG. 4, this involves advancing or retracting the sizing member so that it is located a different distance distal of the fluid inlet port in the needle shaft. This varies the length of the flow path between the sizing member and lumen surface, and therefore the amount of resistance to the flow rather than the size of the flow path and allows for much smaller or finer incremental adjustments. Again, the steps of flowing fluid at a selected pressure and determining the flow rate may be repeated as required. Depending on how much the determined flow rate differs from the desired flow rate and whether the determined flow rate is larger or smaller than the desired flow rate, the position of the sizing member is changed to vary the flow resistance within the needle shaft. For example, if the measured flow rate is only slightly larger than the desired flow, the sizing shaft location may be changed a small amount so that it extends a slightly larger distance distal of the inlet port, increasing flow resistance. On the other hand, if the measured flow rate is somewhat less than the desired flow, the sizing shaft location may be changed so that it extends a reduced distance distal of the inlet port, reducing the resistance to fluid flow. After repeating the steps of flowing fluid at a selected pressure, determining the actual flow rate, and replacing or changing the position of the sizing member, an actual flow rate is achieved that is at or sufficiently near the desired fluid flow rate to provide a relatively predictable and reliable injection flow rate and duration as may be required for the particular medicament and/or circumstances. In general, the present subject matter targets a precision flow rate that is within about 5-10% or less of the desired flow rate, or an overall flow rate variation that is 5% or less. For certain medicament injections contemplated in the present subject matter, a targeted flow rate variation is within about 1-2% or less.

Some non-exclusive examples of possible needle shaft and sizing member sizes contemplated with the present subject matter are: needle shaft OD between about 0.007-0.018 inches, needle shaft ID (lumen diameter) between about 0.003 and 0.010 inches. The sizing shaft OD for potential use with these needle shafts may be in the range of between about 0.005 and 0.009 inches.

One specific calculated example not based on test data is a needle shaft that has an OD that is between about 0.0120-0.0125 inches and an ID that from about 0.0055 to 0.0070 inches and a solid sizing member of about 0.004 inches OD. If the medicament fluid has a viscosity of 1 cP, the needle shaft ID is 0.0055 inches and flow length is 0.385 inches and pressure is 8 psi, the calculated flow rate would be 3.2 ml/min. If a sizing member having an OD of 0.004 inches is inserted the full length of the flow path, the calculated flow rate under the above conditions would be 0.70 ml/min.

Figure 5:
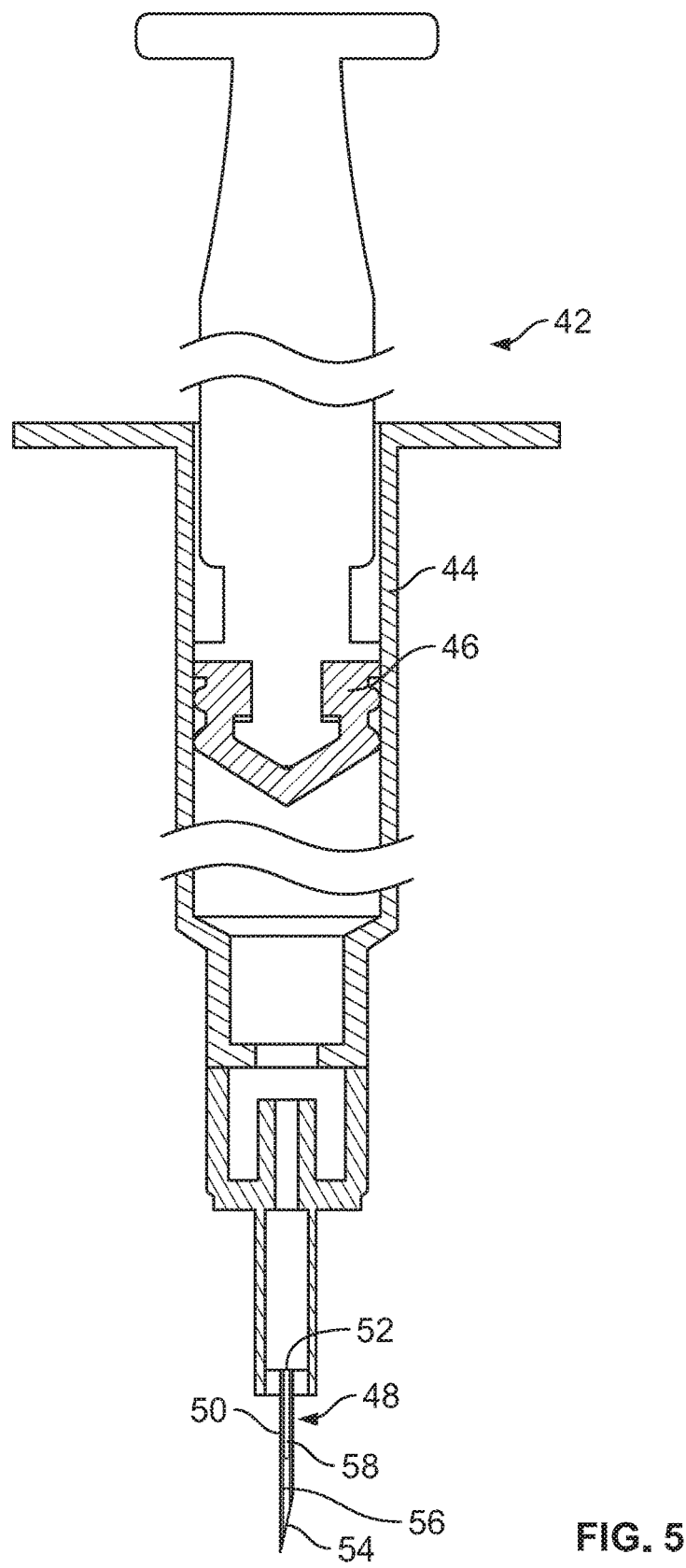
FIG. 5 is a cross-sectional view of another injection device, in the form of a syringe, employing an injection needle in accordance with an aspect of the present subject matter.

While described above in the context of an injection device for relatively automated injection from a pre-filled injection reservoir or bladder, the present subject matter may have application in other settings, and FIG. 5 is one possible alternative. FIG. 5 illustrates a syringe 42 which is standard in its basic construction except for the injection needle in accordance the present subject matter. The syringe has a generally cylindrical barrel 44 with a piston or plunger 46 axially movable in the barrel. The piston is illustrated for manual movement, but the piston 46 could be associated with an automated injection system, sometimes referred to as auto-injector systems, with a driver that moves the piston in at a controlled speed and/or with a controlled force. The syringe could also be pre-filled with the particular drug, biologic or other injectable medicament.

As with the injection needle described above, the syringe 42 has an injection needle 48 with a precision fluid flow path that may be the result of the method described above. The injection needle includes a needle shaft 50 with an open proximal end 52, an open pointed distal end 54 and a fluid flow lumen 56 extending through the full length of the shaft. A sizing member 58 of selected size is fixedly positioned within the lumen and extends a particular distance distal of the proximal end opening into the lumen. The size and location of the sizing member, in accordance with the present subject matter, defines a precision fluid flow path between the surface of the sizing member.

Although, described with reference to the illustrated example, this is only purposes of explanation and not limitation. It is understood that the present subject matter may have application in other circumstances or may be varied in detail without departing from the disclosure herein.

The invention claimed is:

1. A method of making a fluid injection needle having a precision fluid flow path, the method comprising the steps of:
   a. providing an elongated needle shaft terminating in a distal end including a piercing point for piercing the skin of a subject, the needle shaft including an inner surface forming an axially extending bore that defines a fluid flow lumen extending between a distal fluid injection port and a proximal fluid entry port;

b. determining a flow rate for the needle shaft by flowing a selected liquid through the fluid flow lumen between the proximal fluid entry port and the distal fluid injection port at a selected fluid pressure and temperature and measuring a quantity of the liquid passing through the fluid flow lumen over a first particular time period;
c. comparing the determined flow rate to a desired flow rate;
d. selecting a first solid sizing shaft having a first cross-sectional size smaller than the fluid flow lumen based on how much the determined flow rate differs from the desired flow rate;
e. placing the first solid sizing shaft including an outer surface extending axially in the fluid flow lumen a first distance distal of the proximal fluid entry port to define a first fluid flow path in the fluid flow lumen between the outer surface of the first solid sizing shaft and the inner surface of the needle shafts;
f. determining a flow rate for the first fluid flow path by flowing the selected liquid through the first fluid flow path between the proximal fluid entry port and the distal fluid injection port at the selected fluid pressure and temperature and measuring a quantity of the liquid passing through the first fluid flow path over a second particular time period;
g. comparing the determined first fluid flow path flow rate to the desired flow rate;
h. axially adjusting a position of the first solid sizing shaft in the fluid flow lumen by sliding the first solid sizing shaft in the fluid flow lumen so that the outer surface of the first solid sizing shaft extends axially in the fluid flow lumen a second distance distal of the fluid entry port that differs from the first distance distal of the proximal fluid entry port so that an adjusted first fluid flow path is defined;
i. determining a flow rate for the adjusted first fluid flow path by flowing the selected liquid through the adjusted first fluid flow path between the proximal fluid entry port and the distal fluid injection port at the selected fluid pressure and temperature and measuring a quantity of the liquid passing through the adjusted first fluid flow path over a third particular time period;
j. comparing the determined adjusted first fluid flow path flow rate to the desired flow rate.

2. The method of making the fluid injection needle of claim 1 in which the proximal fluid entry port of the needle shaft extends through a side of the needle shaft.

3. The method of making the fluid injection needle of claim 1 in which the distal fluid injection port is located at the distal end of the needle shaft.

4. The method of claim 1 wherein the step of placing the first solid sizing shaft of step e includes securing the first solid sizing shaft within the fluid flow lumen in a fixed non-removable fashion.

5. The method of claim 1 wherein the step of determining the flow rate for the needle shaft of step b includes accumulating the liquid passing through the fluid flow lumen over the particular time period.

6. The method of claim 1 wherein the second particular time period is the same as the first particular time period.

7. The method of claim 6 wherein the third particular time period is the same as the first and second particular time periods.

8. A method of making a fluid injection needle having a precision fluid flow path, the method comprising the steps of:

a. providing an elongated needle shaft terminating in a distal end including a piercing point for piercing the skin of a subject, the needle shaft including an inner surface forming an axially extending bore that defines a fluid flow lumen extending between a distal fluid injection port and a proximal fluid entry port;
b. determining a flow rate for the needle shaft by flowing a selected liquid through the fluid flow lumen between the proximal fluid entry port and the distal fluid injection port at a selected fluid pressure and temperature and measuring a quantity of the liquid passing through the fluid flow lumen over a first particular time period;
c. comparing the determined flow rate to a desired flow rate;
d. selecting a first solid sizing shaft having a first cross-sectional size smaller than the fluid flow lumen based on how much the determined flow rate differs from the desired flow rate;
e. placing the first solid sizing shaft including an outer surface extending axially in the fluid flow lumen a first distance distal of the proximal fluid entry port to define a first fluid flow path in the fluid flow lumen between the outer surface of the first solid sizing shaft and the inner surface of the needle shaft;
f. determining a flow rate for the first fluid flow path by flowing the selected liquid through the first fluid flow path between the proximal fluid entry port and the distal fluid injection port at the selected fluid pressure and temperature and measuring a quantity of the liquid passing through the first fluid flow path over a second particular time period;
g. comparing the determined first fluid flow path flow rate to the desired flow rate;
h. selecting a second solid sizing shaft having a second cross-sectional size that differs from the first cross-sectional size of the first solid sizing shaft based on how much the determined first fluid flow path flow rate differs from the desired flow rate;
i. removing the first solid sizing shaft from the fluid flow lumen;
j. inserting the second solid sizing shaft into the fluid flow lumen so that a second fluid flow path is formed;
k. determining a flow rate for the second fluid flow path by flowing the selected liquid through the second fluid flow path between the proximal fluid entry port and the distal fluid injection port at the selected fluid pressure and temperature and measuring a quantity of the liquid passing through the second fluid flow path over the second particular time period;
l. comparing the determined second fluid flow path flow rate to the desired flow rate;
m. axially adjusting a position of the second solid sizing shaft in the fluid flow lumen by sliding the second solid sizing shaft in the fluid flow lumen so that an adjusted second fluid flow path is defined;
n. determining a flow rate for the adjusted second fluid flow path by flowing the selected liquid through the adjusted second fluid flow path between the proximal fluid entry port and the distal fluid injection port at the selected fluid pressure and temperature and measuring a quantity of the liquid passing through the adjusted second fluid flow path over a third particular time period;
o. comparing the determined adjusted second fluid flow path flow rate to the desired flow rate.

* * * * *